US 6,713,051 B2

(12) United States Patent
Mayes et al.

(10) Patent No.: US 6,713,051 B2
(45) Date of Patent: Mar. 30, 2004

(54) ANTIPERSPIRANT OR DEODORANT COMPOSITIONS

(75) Inventors: Andrew Easson Mayes, Bedford (GB); Anthony Vincent Rawlings, Bebington (GB); Allan Watkinson, Bedford (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 0 days.

(21) Appl. No.: 10/174,245

(22) Filed: Jun. 18, 2002

(65) Prior Publication Data

US 2003/0003068 A1 Jan. 2, 2003

(30) Foreign Application Priority Data

Jun. 18, 2001 (GB) .............................. 0114848

(51) Int. Cl.[7] .............................. A61K 7/32; A61K 7/34; A61K 7/38; A61K 7/00
(52) U.S. Cl. .............................. 424/65; 424/66; 424/68; 424/400; 424/401
(58) Field of Search .............................. 424/65, 66, 68, 424/400, 401

(56) References Cited

U.S. PATENT DOCUMENTS

| 4,724,139 A | 2/1988 | Palinczar ..................... 424/66 |
| 5,254,332 A | 10/1993 | Grezcyn et al. ............... 424/66 |
| 5,260,053 A | 11/1993 | Chappell et al. .............. 424/65 |
| 5,976,514 A | 11/1999 | Guskey et al. ................ 424/65 |
| 5,981,586 A | 11/1999 | Pershadsingh .............. 514/543 |
| 6,083,493 A | 7/2000 | Swaile ......................... 424/65 |
| 6,086,887 A | 7/2000 | Parrott .................... 424/195.1 |
| 6,503,492 B2 * | 1/2003 | McGlone et al. ............. 424/65 |
| 2002/0049250 A1 | 4/2002 | Maignan et al. ............ 514/434 |

FOREIGN PATENT DOCUMENTS

| EP | 888 773 | 1/1999 |
| WO | 93/23008 | 11/1993 |
| WO | 98/32444 | 7/1998 |
| WO | 98/58625 | 12/1998 |
| WO | 99/26597 | 6/1999 |
| WO | 99/47110 | 9/1999 |
| WO | 00/28956 | 5/2000 |
| WO | 01/45663 | 6/2001 |

OTHER PUBLICATIONS

PCT International Search Report in a PCT application PCT/EP 02/05751.
Ishaan Oils Pvt. Ltd. "Hydrogenated Caster Oil Specifications", XP002217334, Oct. 16, 2002.
J. Invest. Dermatol. 111, 1116–1121 (1998); *"Differential Expression of Peroxisome Proliferator—Activated Receptor Subtypes During the Differenitatioh of Human Keratinocytes"*.
Derwent Abstract of EP 888 773—published Jan. 7, 1999.

* cited by examiner

Primary Examiner—Shelley A. Dodson
(74) Attorney, Agent, or Firm—Kevin J. Stein

(57) ABSTRACT

Antiperspirant compositions comprising an astringent aluminum or zirconium salt can suffer from perceived irritancy when applied topically, which can be ameliorated or overcome by incorporating within the composition a PPAR activating fatty acid and/or hydrolyzable precursor thereof such as a triglyceride or ester of the PPAR, especially in an amount selected in the range of from 0.5 to 10 wt %.

The compositions advantageously comprise an activated aluminum salt or aluminum-zirconium glycine complex.

18 Claims, No Drawings

ANTIPERSPIRANT OR DEODORANT COMPOSITIONS

The invention relates to antiperspirant compositions intended for topical application to human skin. In particular, it relates to antiperspirant compositions comprising an agent that is capable of ameliorating or controlling skin irritancy.

BACKGROUND

In many countries, civilised behaviour encourages people to take steps to prevent or control body odours or visible wet patches caused by sweating, particularly in the underarm or on clothing in the vicinity of the underarm. People in some countries prefer to control both sweat and odour, whereas in other countries control of odour alone is favoured.

The antiperspirant market is currently dominated by topically applied products based on aluminium or zirconium salts which are intended to prevent, or at least control, localised perspiration at the skin surface, particularly on the underarm. Such formulations can often simultaneously provide a perceived degree of deodorancy.

Deodorants are formulations that are designed either to mask malodour or to prevent or hinder its formation. The latter method usually comprises reducing and/or controlling the re-growth of the local micro-organism populations, or targeting preferentially those bacteria such as a sub-class of Coryne bacteria which contribute disproportionately to axillary odour generation, or interrupting the pathways by which malodours are formed from secretions. Aluminium or zirconium salts provide deodorancy benefits even at a level below the commonly accepted threshold for significant antiperspiracy to be observed.

Antiperspirant formulations are utilised in many applicator forms e.g. roll-ons, creams or soft solids, gels, firm sticks, aerosols and pump sprays. However all forms can suffer from a number of common disadvantages.

A principal disadvantage of many antiperspirants is that they contain one or more commonly employed ingredients which are perceptably unfriendly to human skin in those areas of the body to which the formulations are normally applied. Such ingredients include in particular the above-mentioned aluminium and zirconium salts, and the effect from those salts can be exacerbated by other ingredients that are usually employed because they demonstrate other attributes which are advantageous or otherwise render the formulation particularly effective. Such essential or otherwise highly desirable or desirable ingredients in aluminium or zirconium salt containing compositions include liquid carriers such as volatile silicones and ethanol, as well as a host of other ingredients commonly employed in such formulations such as fragrance ingredients and emulsifiers. Such ingredients are perceived to exhibit an adverse effect, in particular an irritant effect, on a user's skin following application of the antiperspirant salt-containing formulation.

Skin unfriendliness can be tolerated, at least up to a certain extent which will vary from user to user, but it would be advantageous to identify means of reducing or eliminating the effect. Manifestly, irritation can be ameliorated by lowering the amount of the offending active ingredient in the formulation but a serious drawback of such an approach is that the efficacy of the ingredient is impaired.

It would be desirable to be able to create antiperspirant formulations which were effective and which do not irritate skin, and particularly desirable to provide formulations with a positive skin care benefit too.

It would be desirable to be able to devise antiperspirant formulations which continued to be effective for their primary purpose, that is to say continued to employ known antiperspirant actives displaying the same or similar activity levels, but in which adverse localised skin effects were ameliorated or overcome, and localised skin condition can be improved. The achievement of these outcomes at the same time requires the identification of materials which are not only effective for the secondary purpose but which are not unduly antagonistic towards the constituents which are incorporated to provide or deliver the antiperspirant active, and particularly to avoid or minimise interactions between said materials and said constituents during transportation and storage of formulations containing them.

Various patent specifications have disclosed the incorporation of emollients in antiperspirant formulations.

Many different classes of materials are contemplated within, or U.S. Pat. No. 5,254,332 or WO 00/28956. Emollients are usually regarded as constituents which are non-irritating and at least some of which can soften skin. However, there is no teaching that emollients as a class of materials act as PPAR activating agents, nor any teaching as to how to identify the limited number of emollients which by chance are named and which may be capable of so acting from the preponderant majority of emollients which are named and not capable of so acting.

Similarly, several patent specifications such as WO 98/58625 disclose formulations which are gelled with various gellants, without discussing whether or not they are capable of acting as PPAR activating agents, or indicating how to identify which, if any, of the gellants may be capable of acting as PPAR activating agents in amounts which are less than is required to gel the composition in which it is present, and which are not so capable.

Peroxisome proliferator-activated receptors (abbreviated herein to PPAR) are transcription factors that control lipid metabolism. There are three isotypes PPARα, PPARβ/δ and PPARγ, all of which have been localised in the skin according to Riviers et al, in J. Invest. Dermatol. 111, 1116–1121 (1998). A range of specific fatty acids activates these factors, resulting in anti-inflammatory action, to reduce cutaneous irritation responses, and pro-differentiation/anti-proliferation responses to normalise skin metabolism and provide additional skin-care benefits. In U.S. Pat. No. 5,981,586 Pershadsingh teaches that PPAR ligands can reduce proliferation and inflammation in the skin. In PCT application WO-A-98/32444 Elias et al teaches that PPAR ligands can restore/prevent skin barrier dysfunction. In EP-A-888773 Malnoe et al describes the use of the PPAR activating lipid petroselinic acid in the treatment and prevention of inflammation in superficial tissues. Furthermore, in PCT application WO-A-99/47110, Alaluf et al teach the use of petroselinic acid or glycerides thereof to reduce skin irritation in a treatment for skin intended simultaneously to combat ageing and wrinkling, and also to provide skin lightening properties. In EP-A-709084, Laugier et al describes the use of coriander oil, rich in petroselinic acid, in a skin cosmetic composition for the moisturisation of dry skin. In U.S. Pat. No. 5,260,053, Chappell et al describe deodorant formulations containing inter alia coriander oil, to accomplish odour reduction, by reducing the population of both micrococci and diphtheroids and to mask any lingering androsterone compounds. In DE-A-19883808114, by Grillo Werke et al, there is described a deodorant for domestic, hygiene and industrial use which contains a zinc salt of ricinoleic acid and/or salts of other (un)saturated OH fatty acids with at least 17C. Similarly, deodorising compositions containing zinc ricinoleate are described in FR-A-2311529 to Dart Industries Inc. None of these specifications provide specific teaching in relation to antiperspirant formulations.

In PCT application WO-A-99/26597 (Parrott) teaches that borage oil can be included in an antiperspirant formulation to reduce irritation without reducing the antiperspirant activity, but Parrott does not teach how to locate alternative or improved solutions to the problem, nor how to improve general skin condition.

Although the art does teach the use of a few named emollients in certain skin-care products, research continues in the field to locate alternative or improved systems. The effect of each ingredient of a formulation should not be considered by itself. Its interaction with other ingredients should also be considered to obtain an overall picture. For example, acid neutralisation of antiperspirant actives can result in the de-activation of the antiperspirant active by complexation. Moreover such complexation results in concomitant abrogation of the functionality of the acid as well. Surprisingly, we have found that fatty acids capable of activating PPARs can be incorporated into an antiperspirant cosmetic composition and retain their functionality to produce a composition that has a reduced irritation potential and can also provide additional benefits for underarm skin.

In WO 01/45663 by L'Oreal, published June 2001, i.e. subsequent to the instant priority date, there are described the use of aromatic polycyclic compounds as activators of PPARs-type receptors in a cosmetic or pharmaceutical composition, but once again, there is no disclosure of antiperspirant compositions.

Accordingly, it is an object of the present invention to provide antiperspirant formulations which ameliorate or overcome one or more of the disadvantages described hereinabove, and particularly skin irritation.

More specifically, it is an object of certain embodiments of the present invention to provide antiperspirant formulations in which skin unfriendliness can be ameliorated or eliminated whilst enabling active ingredients to be employed.

It is an object of particular embodiments of the present invention in which topically applied antiperspirant formulations are non irritating.

It is an object of selected embodiments of the present invention to provide topically applicable antiperspirant formulations which provide skin-care benefits in addition to ameliorating or overcoming skin irritancy.

SUMMARY OF THE INVENTION

According to the invention there is provided an antiperspirant cosmetic composition suitable for topical application to human skin, comprising:
  i. an antiperspirant active comprising an astringent aluminium or zirconium salt;
  ii. a carrier for the antiperspirant active; and
  iii. either (a) a PPAR activating fatty acid other than at least 1% by weight of ricinoleic acid or linoleic acid, or (b) a hydrolysable precursor of said fatty acid other than borage oil, castor oil or sunflower seed oil in an effective amount that is insufficient to gel the composition by itself.

In a second and related aspect, the present invention also provides a method of reducing or eliminating skin irritancy arising from topical application of an antiperspirant cosmetic composition comprising an antiperspirant active comprising an astringent aluminium or zirconium salt and a carrier characterised by incorporating in the composition an effective amount of either (a) a PPAR activating fatty acid a) a PPAR activating fatty acid other than at least 1% by weight of ricinoleic acid or linoleic acid or (b) a hydrolysable precursor of a PPAR activating fatty acid other than borage oil, castor oil or sunflower seed oil that is insufficient to gel said composition.

Herein, the term PPAR activating fatty acid includes PPAR$\alpha$, PPAR$\beta$/$\delta$ and PPAR$\gamma$ activating fatty acids. It will be recognised that many PPAR$\alpha$ activating fatty acids are commonly also PPAR$\beta$/$\delta$ and/or PPAR$\gamma$ activating fatty acids.

By an effective amount of a PPAR activating fatty acid or precursor thereof is meant an amount which reduces skin irritancy caused by one or more of the ingredients in the base antiperspirant formulation.

Additional skin benefits can be provided too by employing the PPAR activating agent or precursor, in at least some embodiments.

In a third and related aspect of the present invention there is provided a method for reducing or eliminating body odour and/or controlling sweating comprising topically applying to chosen areas of human skin a composition comprising:
  i. an antiperspirant active comprising an astringent aluminium or zirconium salt;
  ii. a carrier for the antiperspirant active; and
  iii. either a) a PPAR activating fatty acid other than at least 1% by weight of ricinoleic acid
    or (b) a hydrolysable precursor of said fatty acid other than borage oil, castor oil or sunflower seed oil
    in an effective amount that is insufficient to gel the composition by itself.

By the term antiperspirant composition is meant a composition containing an aluminium or zirconium salt that is capable of acting as an astringent, unless specified otherwise.

MORE DETAILED DESCRIPTION OF THE INVENTION, INCLUDING PREFERRED EMBODIMENTS

The invention comprises employing in antiperspirant formulations in which the antiperspirant active is dispensed in a carrier, an effective concentration of a PPAR activating fatty acid or hydrolysable precursor thereof.

One convenient reporter assay for determining whether a fatty acid material is PPAR$\alpha$ activating is based upon the firefly luciferase gene. In such an assay, it is considered herein to be PPAR$\alpha$ activating fatty acid if it produced at least a 1.5 times activation compared with the vehicle control, when administered at 100 $\mu$M. More preferably, a PPAR$\alpha$ activating ligand produces at least a 1.5 fold induction at 50 $\mu$M; more preferably still at least a 1.5 fold induction at 25 $\mu$M; and even more preferably at least a 1.5 fold induction at 10 $\mu$M. Naturally, the ligands continue to induce when employed at a higher administration level.

We have found that it is not essential to provide the fatty acid in free form. Additionally or alternatively, the PPAR fatty acid can be incorporated into the formulation as a hydrolysable precursor, such as particularly a triglyceride or ester. This is especially convenient for underarm formulations, because of the presence of commensal skin bacteria in particularly high numbers in the underarm compared with general body areas. Such bacteria can hydrolyse triglycerides and esters efficiently on the skin and thereby release fatty acids; (Marples, R. Cur. Med. Res. Opin. 7, Suppl. 2, pp. 67–70 (1982)).

It is particularly desirable to select PPAR fatty acids or precursors thereof which are unsaturated, and especially those containing an hydroxyl and/or methyl side chain. Many such acids contain from 14 to 30 carbons.

Examples of PPAR fatty acids with demonstrated PPAR activating activity are:

i) cis-parinaric acid
ii) cis-9-trans-11 conjugated linoleic acid
iii) columbinic acid
iv) docosahexaenoic acid
v) eicosapentanoic acid
vi) hexadecatrienoic acid
Vii) linolenelaidic acid (isomer of linolenic acid)
Viii) petroselinic acid
ix) pinolenic acid
x) punicic acid
xi) ricinoleic acid
xii) ricinolaidic acid (isomer of ricinoleic acid)
xiii) stearidonic acid
xiv) trans-10-cis-12 conjugated linoleic acid
xv) 7-trans octadecanoic acid
xvi) vaccenic acid Potential source of hydrolysable PPAR precursors include triglycerides such as coriander seed oil for petroselinic acid, impatiens balsimina seed oil, parinarium laurinarium kernel fat or sabastiana brasilinensis seed oil for cis-parinaric acid, dehydrated castor seed oil for conjugated linoleic acids, and aquilegia vulgaris oil for columbinic acid.

If a single hydrolysable precursor of a PPAR activating fatty acid is employed, it specifically excludes borage oil, castor oil and sunflower seed oil.

Desirably, the PPAR acid contains 16 or 18 carbon atoms. Most preferred PPAR acids are olefinically unsaturated, and especially preferably, comprise mono, di or tri unsaturation. Many most desirable PPAR activating acids are not only unsaturated, but also are C16 or C18 acids. An alternative PPAR acid (xvii) comprises 12-hydroxystearic acid, sometimes abbreviated to 12-HSA which is effective for the present purpose at a concentration below that which is needed to form a gelled formulation.

The proportion of fatty acid PPAR ligands in the invention is at least the minimum proportion which demonstrates a reduction of irritancy and/or improvement in skin condition, compared with the same composition in the absence of the PPAR ligand. As would be expected, such minimum proportion will not only vary from compound to compound but also will depend on whether the acid is employed in free form or introduced via its precursor. The minimum proportion can be determined by a patch test method described subsequently herein. In many formulations, the PPAR fatty acid or precursor is chosen in the range of from at least 0.025%, and preferably from 0.05% by weight, and in general not more than 20% by weight. In a number of preferred formulations, it is convenient to employ a concentration of PPAR fatty acid or precursor of at least 0.1% up to 5%, such as 0.2 to 1% by weight.

If desired, the PPAR acid or precursor can comprise any combination of two or more PPAR acids or precursors, provided that at least one of them satisfies the condition that it is either (a) a PPAR activating fatty acid other than at least 1% by weight of ricinoleic acid or linoleic acid or (b) a hydrolysable precursor of a PPAR activating fatty acid other than borage oil, castor oil or sunflower seed oil. The second PPAR acid or precursor can be selected from all PPAR acids and their precursors, including ricinoleic acid, linoleic acid castor oil, sunflower seed oil and borage oil. The weight ratio of constituents of such a combination of PPAR acids or precursors can often be chosen in the range of 5:1 to 1:5, such as from 3:1 to 1:3, and particularly at about 2:1, about 3:2, about 1:1, about 2:3 or about 1:2. Desirably, the combination comprises at least two PPAR acids selected from examples i) to xvii) hereinabove, or their glyceride precursor with the aforementioned weight ratios or within the ratio ranges of 5:1 and 1:5, and preferably 1:1.

Some preferred combinations comprise:

petroselinic acid and 12 HSA petroselinic acid and petroselinic acid and linoleic acid precursor (Sunflower oil and/or Borage oil)

petroselinic acid and pinolenic acid petroselinic acid &and pinolenic acid precursor (pine nut oil)

petroselinic acid and cis parinaric acid pinolenic acid and 12 HSA pinolenic acid and linoleic acid pinolenic acid and linolenic acid 12-HSA and linoleic acid 12-HSA and linolenic acid cis parinaric acid and 12-HSA cis parinaric acid and linoleic acid cis parinaric acid and linolenic acid cis parinaric acid & pinolenic acid An antiperspirant composition according to the invention comprises an antiperspirant active which comprises an astringent aluminium or zirconium salt. The proportion of antiperspirant active present in the composition according to the invention may be from 1–35% by weight of the composition, preferably at least 5% by weight and more preferably 15–30% by weight of the base composition. A base composition herein excludes any propellant which may be employed.

Examples of suitable actives include aluminium salts, zirconium salts, aluminium and/or zirconium complexes, for example aluminium halides, aluminium hydroxy halides, zirconyl oxyhalides, zirconyl hydroxyhalides, and mixtures thereof. Specific examples include activated aluminium chlorohydrate, aluminium chlorohydrate, aluminium pentachlorohydrate and aluminium zirconium chlorohydrate. Useful zirconium salts include zirconium hydroxy-chloride and zirconium oxychloride. Other generally used actives will be known to those skilled in the art. Preferred actives include ZAG (Zirconium Aluminium Glycine), AAZG (Activated Aluminium Zirconium Glycine), and AACH (Activated Aluminium Chorohydrate). The antiperspirant active can be present in particulate form whereupon it is normally suspended in a suitable carrier fluid, which usually is water-immiscible, and which can be structured or thickened. Alternatively the active can be dissolved in a polar solution, such as for example in aqueous solution or in a polar low weight polyhydric alcohol such as propylene glycol, advantageously 30 to 60% by weight solution.

The compositions according to the present invention can also comprise 0.01 to 90% of a deodorant active. The deodorant active used in the cosmetics of the invention can be any deodorant active known in the art such as alcohols, in particular aliphatic monohydric alcohols such as ethanol or propanol, antimicrobial actives such as polyhexamethylene biguanides eg those available under the trade name Cosmocil™ or chlorinated aromatics, eg triclosan available under the trade name Irgasan™, non-microbiocidal deodorant actives such as triethylcitrate, bactericides and bacteriostatis. Yet other deodorant actives can include zinc salts such as zinc ricinoleate.

In some embodiments, the deodorant active comprises an aluminium and/or zirconium salt or complex as described hereinabove in relation to providing antiperspirancy, but at a concentration such as from 0.1 to 6% by weight which imparts deodorancy without always meeting national minimum standards for antiperspirancy.

The carrier material for the compositions according to the invention can comprise one or more of volatile carrier fluids, one or more of non-volatile emollients, and it can be structured or thickened by one or a combination of thickener and/or structurant materials if required. The carrier material, including, where relevant, carrier materials providing additional properties such as emolliency, can often comprise up to about 99 wt %, in many instances from 5 to 90 wt % and particularly from 10 to 70 wt % of the composition, or of the base composition, if mixed subsequently with a propellant. Where the composition comprises both hydrophylic and hydrophobic phases, the weight ratio of the two phases is often in the range of 10:1 to 1:10. Aerosol compositions according to the present invention can conveniently be obtained by introducing a base formulation as described herein that is free from propellant and at least 0.7 times and often 1.5 to 20 times its weight of propellant into a suitable aerosol dispenser.

The antiperspirant composition can comprise a mixture of particulate solids or a suspension of solids in a liquid medium, which can be thickened to reduce the rate of segregation, or structured to produce a cream (soft solid) or solid. Alternatively the composition can comprise a mixture of liquid constituents, including a solution of an active in a carrier, such a composition often adopting the form of an oil-in-water or water-in-oil emulsion, which may be thickened or gelled.

The carrier material, which may be a fluid or a mixture of fluids, is often selected according to the physical form of the cosmetic composition, e.g. volatile low viscosity silicones, low molecular weight hydrocarbons, alcohols and water, and can be selected by those skilled in the art to provide appropriate physical and sensory properties for the product. It will be understood that certain fluid alcohols such as in particular ethanol can constitute both a carrier and a deodorant active simultaneously, though advantageously formulations containing such a material also contain an additional deodorant and/or antiperspirant active.

Volatile silicones are usually selected from cyclic polysiloxanes containing from 3 to 8 dialkylsilicone groups, especially dimethylsilicone groups and particularly 4 or 5 dimethylsilicone groups. Other useful volatile silicones can comprise linear polysiloxanes, preferably containing 4 or 5 alkylsiloxane groups, including terminal groups. Low molecular weight liquid hydrocarbons can comprise paraffin oils. Suitable alcohols can comprise monohydric alcohols, such as C3 to C10 aliphatic alcohols, dihydric alcohols such as glycol or propylene glycol or polyhydric alcohols such as glycerol or sorbitol. Carrier materials can provide additional desirable properties, such as polyhydric alcohols for example glycerol can act as a moisturising agent and volatile cyclomethicones can act as emollients.

The non-volatile emollient, if used in the composition, may consist of a single emollient compound or a mixture of emollients. Such emollients often have a solubility parameter of below 10 and many of from 5.5 to 9. They can typically include saturated fatty acids and fatty alcohol esters, ethers containing aliphatic and a polyalkylene group, hydrocarbons, water insoluble ethers, mineral oils and polyorganosiloxanes, and mixtures thereof.

Non-volatile silicones are often polyalkylsiloxanes, polalkylarylsiloxanes or polyethersiloxanes having a viscosity of above 10 mPa·s, such as up to about $5 \times 10^6$ mPa·s at 25° C., including polymethylphenylsiloxanes or dimethylpolyoxyalkylene ether copolymers.

Emollient aliphatic esters, often containing from about 12 to 25 carbons, and preferably one substituent containing a chain of at least 12 carbons. Examples include cetyl palmitate, butyl myristate, glyceryl stearate and propylene glycol monolaurate. The composition cam comprise a liquid aliphatic ether which can provide emolliency, such as ethers derived from polyalkyene glycols and a low weight (eg up to C6) alcohol, such as polypropylene glycol (10-15) butyl ether.

The total amount of emollient materials within the composition, excluding PPAR fatty acid and precursor thereof, is often within the range of from 1 to 70 wt %.

The thickening or structurant agent, when required, is selected according to the product form of the cosmetic composition. The thickening or structuring agent can be organic (monomeric or polymeric) or inorganic and is usually chosen depending on the physical nature of the liquid phase to be thickened or structured, such as whether it is hydrophobic or hydrophylic. The amount is normally selected in order to attain the desired viscosity for the liquid or cream or desired resistance to penetration of a solid containing the PPAR fatty acid or precursor thereof in accordance with the present invention.

The thickener or structurant can be any of a number of materials, including, for example, waxy structurants for a formulation containing a water-immiscible phase including hydrogenated vegetable oil, hydrogenated castor oil, fatty acids, such as 12-hydroxystearic acid (12-HSA), or ester or amide derivatives of such acids, beeswax, paraffin wax, microcrystalline waxes, silicone wax, and fatty alcohols, such as stearyl alcohol. The structurant can also be a fibre-forming gellant, of which 12-HSA is an example. Other examples include N-acyl amino acid amides and esters, including particularly GP-1 (N-Lauroyl-L-glutamic acid di-n-butylamide), lanosterol, combinations of a sterol and a sterol ester, such as especially β-sitosterol and γ-oryzanol, a polyesterified cellobiose, especially with a C8 to C10 aliphatic acid, threitol esters or and selected secondary amides of di or tri basic carboxylic acids, (eg 2-dodecyl-N,N'-dibutylsuccinimide) by themselves or in combination.

Polymeric materials for thickening include polymers such as polyamides, hydroxypropylcellulose, and natural or synthetic gums, such as polyglycerides including agar, agarose, pectin, or guars or mixtures or combinations thereof. One class of materials worthy of attention for thickening a water-immiscible phase comprises derivatives of hydrolysed starch or other polysaccharides, including in particular esterified dextrins, such as dextrin palmitate. A further class of polymers that is particularly directed to structuring an oil phase containing a silicone oil comprises polysiloxane elastomers. Suspending agents such as silicas or clays such as bentonite, montmorillonite or hectorite, including those available under the trademark Bentone can also be employed to thicken liquid compositions according to the invention. The composition can be thickened with non-polymeric organic gellants, including selected dibenzylidene alditols (eg dibenzylidene sorbitol).

The amount of structurant or thickening agent that can be employed in the invention compositions will depend upon the viscosity of a fluid formulation or extend of hardness of a solid formulation that the producer wishes to attain. The amount to be employed will in practice also vary depending on the chemical nature of the structurant or thickening agent. In many instances, the amount of structurant or thickening agent will be selected in the range of from 0.1 to 25 wt %, and particularly from 1 to 15 wt %.

The composition according to the invention can optionally comprise other ingredients, in addition to those already identified, depending on the nature and form of the finished product.

Other ingredients contemplated within the personal deodorant or antiperspirants art can also be included in the compositions according to the invention. These include, for example, surfactants/wash-off agents, fillers, fragrances, preservatives and colouring agents. Such ingredients and their amounts of use are usually selected according to the physical and chemical form of the cosmetic composition.

Surfactants can comprise optionally up to 15%, more commonly up to 5% by weight of the total product, and are particularly useful in formulating emulsion antiperspirant compositions, for example for use as pump spray or roll-on formulations. However for other product types, it is preferred that the composition contains less than about 8% by weight of surfactants. Non-ionic surfactants are particularly preferred. It is often convenient to select a mixture of surfactants, such as one having a comparatively high HLB value, eg 8 to 18, and one having a comparatively low HLB value, eg 2 to 8, which can be introduced in suitable relative proportions to attain an average HLB value of about 6 to 12.

Many suitable nonionic surfactants are selected from nonionic esters, ethers or amine oxides having an appropriate HLB value. Many preferred ionic surfactants comprise a polyoxyalkylene moiety, especially a polyoxyethylene moiety eg 2 to 80, especially 5 to 60 oxyethylene units, or possibly with a polyoxypropylene content, to provide hydrophilicity. Other moieties providing hydrophilicity include polyhydric alcohols such as sorbitol or glycerol. The hydrophobic moiety is commonly derived from aliphatic alcohols or acids or amines containing about 8 to 50 carbons and particularly 10 to 30 carbons. Examples of suitable nonionic surfactants include ceteareth-10 to -25, ceteth-10-25, steareth-10-25, and PEG-15-25 stearate or PEG-8 distearate. Other suitable examples include C10-C20 fatty acid mono, di or tri-glycerides. Further examples include C18-C22 fatty alcohol ethers of polyethylene oxides (8 to 12 EO).

Examples of surfactants which typically have a low HLB value, and often of from 2 to often comprise mono or possibly di-fatty acid esters of polyhydric alcohols such as glycerol, sorbitol, erythritol or trimethylolpropane, including cetyl, stearyl arachidyl and behenyl derivatives.

Fillers can comprise up to about 20%, more commonly up to 10% of the base composition and can act as supports for liquid ingredients. Suitable fillers include aluminium stearate, aluminium tri-stearate, calcium stearate, talc or finely divided polyethylene, an example of which is ACUMIST B18. The latter can also enhance skin feel properties.

Fragrances, when present, typically comprise up to about 4% of the total product and often from 0.1 to 1.5%. Colouring agents and preservatives can be added as desired.

Other optional ingredients are other cosmetic adjuncts conventionally employed or contemplated for employment in antiperspirant products.

The ingredients which can optionally be present in the composition carrier can conveniently form the balance of the composition.

Propellants commonly employable in aerosol compositions herein commonly comprise hydrocarbons or halohydrocarbons such as fluorohydrocarbons, having a boiling point of below 10° C. and especially those with a boiling point below 0° C. It is especially preferred to employ liquified hydrocarbon gasses, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane. Other or additional propellants include fluorinated low molecular weight hydrocarbons. Yet still other propellants can include volatile ethers or carbon dioxide.

The relative weight proportions of propellant and base composition is often selected at least 40:60 and particularly at least 60:40. The proportions in many embodiments are up to 99:1 and particularly up to 95:1. Commonly, proportions are selected in the range of at least 70:30 and in the same or other formulations the proportions are up to 90:10.

Compositions according to the invention can be provided in any form of a product suited to or adapted for topical application to human skin, and is usually contained in a suitable holder or dispenser to enable it to be applied to the selected area of the skin, particularly the underarm, where control of perspiration and/or deodorancy is desired.

Having described the invention in general terms, specific embodiments thereof will now be described in greater detail by way of example only.

EXAMPLE 1

PPARα Reporter Gene Assay

Fatty acids were screened to identify PPAR activating fatty acids using a reporter assay.

This assay relied on ligands binding to and activating the PPARα protein, which, in turn, activated genes under the control of PPAR response elements (PPRE). In the assay, the firefly luciferase gene was cloned behind a promoter containing 3 copies of the fatty acid binding protein PPRE. The level of luciferase activity observed was in direct relationship to and hence indicated the level of PPAR activation.

The assay was performed by transient transfection of Cos-7 cells with a mixture of four DNA plasmids. These were:

1) PPAR reporter gene construct (Modified pNF-KB-luc reporter vector (Firefly luciferase reporter vector commercially available form Clontech (NF-kB response element, TK minimal promoter, luc$^+$, f1 origin, pUC origin, amp$^r$)). A tandem repeat of 3 PPAR response elements (PPREs) corresponding to the PPRE found in the fatty acid binding protein promoter was inserted upstream of the minimal TK promoter to replace the NF-κB response element);

2) 2) Over-expressing PPARα construct (Modified pcDNA3.1(−) vector (A mammalian expression vector commercially available from Invitrogen (CMV promoter, f1 origin, SV40 origin, ColE1 origin, neo$^r$, amp$^r$)). The coding region of a human PPARα cDNA was inserted downstream of the CMV promoter of pcDNA3.1 (−)). 3) Over-expressing RXRα construct (Modified pRSVcat (RSV LTR, pMB1 origin, amp$^r$) vector (Proc, Natl, Acad, Sci, USA 79 6777–6781). The coding region of a human RXRα cDNA has been inserted downstream of the RSV promoter. (Gift of V. K. K. Chatterjee, Addenbrooke's Hospital, Cambridge)) 4) Control luciferase construct (pRL-TK Renilla luciferase reporter vector commercially available from Promega (HSV-TK promoter, T7 promoter, Rluc$^+$, ori, amp$^r$)). For the transfection, DNA was made up as a mix of PPAR reporter gene: PPARα: RXRα: control in the ratio 40:4:3:3.

Cos-7 cells were grown in Dulbecco's modified Eagle's Medium, also herein referred to as DMEM with 10% foetal calf serum, herein also referred to as FCS at 37° C., 5% $CO_2$ to 80% confluency. Cells were then plated out in 24 well plates at 50,000 cells per well and incubated overnight in DMEM with 10% FCS at 37° C., 5% $CO_2$. Cells were then transfected using the LipofectAMINE reagent (GibcoBRL). For each well 0.4 µg of DNA mix (in 25 µl of DMEM) was incubated with 1 µl LipofectAMINE (in 25 µl of DMEM) for 45 minutes. The mixture was then made up to 250 µl per well and added to the cells, which had been washed with 1 ml of DMEM. Cells were then incubated for 5 hours at 37° C., 5% $CO_2$ and 250 µl DMEM with 10% SBCS (charcoal stripped bovine calf serum) added. Cells were incubated for 18 hours at 37° C., 5% $CO_2$ before being treated with the appropriate compound/extract. Test compounds were made up as 1000× stocks (in DMSO or ethanol as appropriate) and diluted into DMEM with 10% SBCS (500 µl per well) immediately before being added to cells. Each treatment was performed in triplicate. The transfection mix was removed from the cells and replaced with the treatment mix, and incubated for 24 hours at 37° C., 5% $CO_2$. Cells were washed with 1 ml of PBS (without calcium or magnesium) and then lysed with 100 µl per well of 1× Passive Lysis Buffer (as supplied with Promega Dual Luciferase assay kit). Lysis was allowed to continue for 15 minutes and then the lysate was assayed for Firefly and Renilla luciferase activity using the Promega Dual Luciferase assay kit. For the assay, 20 µl of lysate was taken and assayed as described in the kit instructions using a MLX microtiter™ plate luminometer (Dynex).

Firefly luciferase activity (PPAR driven) was normalised against the Renilla luciferase value for that well and the mean calculated for the three wells treated with the same agent. Activity was then expressed as fold activation over the vehicle (DMSO or ethanol) control values for that particular plate. The pharmaceutical PPARα ligand WY14, 643 was included as a positive control.

According to the above-described reporter assay, a fatty acid in this Example passes the assay, ie it is a PPARα activating fatty acid which produces activation that is greater than that from oleic acid when administered at 100 µM, which commonly means greater than 1.57 times activation compared with the vehicle control, when administered at 100 µM.

The lowest tested administration level is shown at which the test material passed and also the lowest administration level at which superior activity [super] (50% higher—at least 2.25 times PPARα activation) or more superior activity [MS] (100% higher—at least 3 times PPARα activation) was achieved. The results of the screening assay are summarised in Table 1 below:

TABLE 1

| Material | Pass at | Result at | |
|---|---|---|---|
| WY14,643 (positive control) | 10 µm | super | 100 µm |
| 12-hydroxystearic acid | 10 µm | MS | 25 µm |
| Arachidonic acid | 25 µm | | |
| cis 13,16 docosadienoic acid | 10 µm | | |
| cis parinaric acid | 10 µm | super | 25 µm |
| cis-11 eicosenoic acid | 100 µm | | |
| cis-11,14,17 eicosatrienoic acid | 100 µm | MS | 100 µm |
| cis-11,14-eicosadienoic acid | 10 µm | MS | 100 µm |
| cis-13,16,19 docosatrienoic acid | 100 µm | | |
| cis-13-octadecenoic acid | 50 µm | | |
| cis-15-octadecanoic acid | 100 µm | | |
| cis-4,7,10,13,16,19 docosahexenoic acid | 10 µm | | |
| cis-5 eicosenoic acid | 10 µm | MS | 100 µm |
| cis-7,10,13,16 docosatetraenoic acid | 100 µm | super | 100 µm |

TABLE 1-continued

| Material | Pass at | Result at | |
|---|---|---|---|
| cis-8,11,14 eicosatrienoic acid | 100 µm | super | 100 µm |
| CLA (50:50 mod2:mix2) | 50 µm | MS | 100 µm |
| CLA (c9, t11) | 10 µm | super | 25 µm |
| CLA (t10, c12) | 50 µm | super | 100 µm |
| CLA (t9, t11) | 50 µm | MS | 100 µm |
| Columbinic acid | 10 µm | super | 25 µm |
| Elaidic acid | 100 µm | | |
| Hexadecatrienoic acid | 10 µm | super | 10 µm |
| Linoleic acid | 10 µm | super | 100 µm |
| Linolelaidic acid | 25 µm | | |
| Linolenelaidic acid | 25 µm | super | 25 µm |
| Palmitoleic acid | 50 µm | | |
| Petroselaidic acid | 50 µm | super | 100 µm |
| Petroselinic acid | 10 µm | MS | 100 µm |
| Pinolenic acid | 10 µm | | |
| Punicic acid | 25 µm | | |
| Ricinolaidic acid | 10 µm | MS | 25 µm |
| Ricinoleic acid | 10 µm | | |
| Stearidonic/octadecatetraenoic acid | 25 µm | super | 25 µm |
| Stearolic acid | 10 µm | | |
| Sunflower oil fatty acids | 25 µm | super | 50 µm |
| trans vaccenic acid | 10 µm | | |
| trans-12-octadecenoic acid | 100 µm | | |
| Trans-13-octadecenoic acid | 10 µm | | |
| Trans-7-octadecenoic acid | 10 µm | MS | 10 µm |
| Base-line Oleic acid (1.57 at 100 µM) | base | | |

EXAMPLE 2

In Example 2, Skin Organotypic Culture Analysis of Petroselinic acid (herein abbreviated to PSA) was employed to show anti-inflammatory action against antiperspirant-induced irritation.

Methods

In this Example, skin organotypic cultures (Epiderm™, MatTek, USA) were treated topically with a cosmetic lotion containing an antiperspirant (AP formulation) summarised herein in Table 2, and the petroselinic acid was introduced into the medium. The cultures were then incubated at 37° C., 5% $CO_2$, and 95% relative humidity (standard cell culture conditions) for 24 h. The culture medium was assayed for the pro-inflammatory cytokine interleukin-6 (IL-6) and after washing to remove the AP formulation, the viability of the culture was determined using the Thiazoyl blue (MTT) assay (Mosmann, T. J. Immunol. Methods 65, p55 (1983). IL-6 was determined using an Immunoassay (Quantikine, R&D systems).

IL-6 Assay Results

The results are summarised in Table 2 below.

Petroselinic acid (500 µM) was found to significantly decrease AP-induced IL-6 release from the cultures using Dunnet's test with a significance value of $p<0.05$. The reduction in the pro-inflammatory cytokine IL-6 indicates that the PSA will inhibit AP-induced irritation. Culture viability of treatment with AP formulation alone was not significantly different from those of the AP formulation and petroselinic acid treatment.

TABLE 2

| Trade Name | INCI Name | Supplier | % w/w |
|---|---|---|---|
| Rezal 67 | Al—Zr Pentachlorohydrate (40%) | Reheis | 50.00 |
| Distilled Water | Water | NWW | 35.95 |
| DC245 | Cyclomethicone | Dow Corning | 4.00 |

TABLE 2-continued

| Trade Name | INCI Name | Supplier | % w/w |
|---|---|---|---|
| Emulgade SE | Glyceryl Stearate, Ceteareth-20, Ceteareth-12, Cetearyl Alcohol, Cetyl Palmitate | Cognis | 2.00 |
| Structure Solanance | Amphoteric Potato Starch | National Starch | 1.00 |
| | Parfum | | 1.00 |
| Polawax GP200 | Cetearyl Alcohol, PEG 20 Stearate | Croda | 0.65 |
| Cutina MD | Glyceryl Stearate | Cognis | 1.00 |
| Eumulgin B2 | Ceteareth-20 | Cognis | 0.40 |
| Eutanol G | Octyldodecanol | Cognis | 0.50 |
| Glycerol | Glycerine | Unichema | 4.00 |

EXAMPLE 3

In this Example, a human Patch Test Irritation Analysis of Petroselinic acid was carried out to show anti-irritant action in vivo.

Methods

Patch tests were performed on mixed panel of 50 volunteers with age ranges between 18 and 55, using a double-blinded protocol with randomised patch sites. Samples (20 mg) were applied to a filter paper that was placed within a Finn™ chamber (0.8 cm internal diameter). The chambers were then attached to the volar forearm using Scanpore™ tape (Norgesplater, Nor.) and left for 47 h. At the end of the 47 h period, the patches were removed and the site was left open for 5 h, Whereupon any dryness and erythema associated with the patch was visually assessed and scored by trained assessors in accordance with the assessment criteria indicated hereinafter in Table 3.

Results

The results are summarised in Table 3 below.

TABLE 3

| Patch Treatment | Mean Irritation Score |
|---|---|
| Prototype pump spray | 0.62 |
| Prototype pump spray + 0.25% petroselinic acid | 0.49 |
| No Treatment | 0.46 |

The antiperspirant prototype pump spray formulation produced a significant increase in irritation score. This was significantly mitigated by the incorporation of 0.25% petroselinic acid into the formulation. Statistical analysis was performed using a Wilcoxon signed rank test with a significance level of 5%. The conclusion from this experiment is that the irritation induced by patch testing the antiperspirant prototype pump spray was reduced significantly by the petroselinic acid.

Patch Grading Scale

TABLE 4

| Grade | Description |
|---|---|
| 0.0 | No apparent cutaneous involvement. |
| 0.5 | Faint, barely perceptible erythema or slight dryness |
| 1.0 | Faint but definite erythema, no eruptions or broken skin or no erythema but definite dryness; may have epidermal fissuring. |
| 1.5 | Well defined erythema or faint papules with definite dryness, may have epidermal fissuring. |
| 2.0 | Moderate erythema, may have very few papules or deep fissures, moderate to severe erythema in the cracks. |
| 2.5 | Moderate erythema with barely perceptible oedema or severe erythema not involving a significant portion of the patch (halo effect around the edges), may have a few papules or moderate to severe erythema. |
| 3.0 | Severe erythema (beet redness), may have generalised papules or moderate to severe erythema with slight oedema (edges well defined by raising). |
| 3.5 | Moderate to severe erythema with moderate oedema (confined to patch area) or moderate to severe erythema with isolated eschar formations or vesicles. |
| 4.0 | Generalised vesicles or eschar formations or moderate to severe erythema and/or oedema extending beyond the area of the patch. |

EXAMPLE 4

In this Example, skin Organotypic Culture Analysis was conducted using trans-10-cis-12 conjugated linoleic acid.

Methods

In this Example, skin organotypic cultures (Epiderm™, MatTek, USA) were treated topically with the above-identified AP formulation and the trans-10-cis-12 conjugated linoleic acid (TC CLA) was introduced into the medium. The cultures were then incubated at 37° C., 5% $CO_2$, and 95% relative humidity (standard cell culture conditions) for 24 h. The culture medium was assayed for the pro-inflammatory cytokine interleukin-6 (IL-6) and after washing to remove the AP formulation, the viability of the culture was determined by the method described in Example 2. The results are summarised in Table 5 below IL-6 Assay Results TC CLA (5 and 500 $\mu$M) was found to significantly decrease AP-induced IL-6 release from the cultures using Dunnet's test with a significance value of $p<0.01$. The reduction in the pro-inflammatory cytokine IL-6 indicates that the TC CLA is able to inhibit AP-induced irritation. Culture viability of AP treatment alone was not significantly different from those of AP and petroselinic acid treatment.

TABLE 5

| Treatment | IL-6 pg/ml | sd | n |
|---|---|---|---|
| Nil | 51.7 | 6.3 | 4 |
| AP | 118.8 | 35.3 | 4 |
| 5 $\mu$M TC-CLA + AP | 59.6 | 12.3 | 4 |
| 500 $\mu$M TC-CLA + AP | 57.1 | 16 | 4 |

EXAMPLE 5

In this Example, the hydrolysis of PPAR fatty acid containing triglycerides by common skin bacteria found in human underarm was demonstrated.

The ability of representative lipolytic cutaneous bacteria (Table B) to hydrolyse the triglyceride forms of petroselinic acid and conjugated linoleic acid (tri-CLA), liberating the corresponding free fatty acids (FFAs) was determined.

Representative Lipase-Active Skin Bacteria

TABLE B

| Genus/Group | Species | 994 Code |
|---|---|---|
| Corynebacterium | unspeciated | G42 |
| Staphylococcus | S. epidermidis | DH1 |
| Propionibacterium | P. acnes | G63 |

Method

Microbial biomass was generated by growth of each culture in 2×500 ml LIPMED™ medium (20 g/l Tryptone™ Soya Broth; 10 g/l Yeast Extract; 2.5 g/l Tween 80™), initially for 48 h. At this point, high-oleate sunflower oil (abbreviated herein to HOSF) was added to stimulate lipase activity and the cultures were incubated for a further 48 h before being harvested and washed in $KP_i$ (pH 8.0) buffer. Resuspended cell pastes were adjusted to pH 8.0 prior to determination of dry weights and lipolytic activity.

To determine the lipolytic activity of the cell pastes on the test, triglycerides (tripetroselinin & tri-CLA), as well as crude triolein (HOSF) which was included as a positive control, the amount of free fatty acids (abbreviated to FFA) released was determined by Gas Chromatography analysis.

Each assay consisted of 3 ml cell paste, to which was added 2 ml Reaction Mixture, containing 5% (v/v) triglyceride & 16.67% (v/v) Emulsification Reagent (17.9 g/l NaCl; 0.41 g/l $KH_2PO_4$; 540 ml/l Glycerol; 6.0 g/l Gum Arabic; adjusted to pH 8.0). All assays were set up in duplicate, along with cell-free controls, and incubated at 30° C. with agitation (100 rpm), for 4 h. At the end of the experiment, the assays were stored at 4° C. for 72 h before being processed for analysis.

Liberation of FFA from the tested triglycerides was quantitatively determined by capillary Gas chromatograph (herein abbreviated to GC) analysis. In an internal standard, (1.0 mg/ml lauric acid) was added to each assay and the culture medium acidified (pH~2) by the addition of HCl. Liquid-liquid extraction was carried out using 2 vol (10 ml) ethyl acetate; organic and aqueous phases were resolved by centrifugation (2000 rpm, 3 min). 2.0 ml of each organic (upper) phase was then transferred to a sampling tube prior to analysis on a Perkin Elmer 8000™ (Series 2) GC fitted with a 15 m×0.32 mm (internal diameter) FFAP (nitroterephthalic acid modified PEG/siloxane copolymer) fused silica capillary column (film thickness 0.25 $\mu$m) (Quadrex). This column was attached to the split-splitless injector and flame ionisation detector (FID) of the GC; injector and detector temperatures were each 300° C. Carrier gas for the column was helium (6.0 psi), while hydrogen (17 psi) and air (23 psi) supplied the FID. The temperature programme for FFA analysis was 80° C. (2 min); 80–250° C. (20° C./min); 250° C. (8 min). Sample size for injection was 0.5–1.0 $\mu$l. FFA levels in the flasks were quantified by comparison of peak areas with known levels of both internal (lauric acid) and external (oleic, petroselinic & conjugated linoleic acids) standards.

Results

Results are expressed as mg FFA liberated per g cell dry weight biomass (mg FFA/g CDwt) over the 4 h experimental incubation time. In each case, only the predominant FFA hydrolysed was quantified (ie. oleic acid from HOSF; petroselinic acid from tripetroselinin; CLA from tri-CLA); consequently, it is likely that the total FFA is higher in at least some of these results, and hence the true extent of lipase activity is underestimated—(eg. significant levels of other fatty acids are present in HOSF). The results are summarised in Table 6 below.

TABLE 6

| Bacterium | Substrate | Mean Lipase Activity (mg FFA/g CDwt) |
|---|---|---|
| Corynebacterium (A) sp. G42 | HOSF (Triolein) | 1.52 |
| | Tripetroselenin | 6.26 |
| | tri-CLA | 2.23 |
| S. epidermidis DH1 | HOSF (Triolein) | 36.0 |
| | Tripetroselenin | 114.4 |
| | tri-CLA | 59.9 |
| P. acnes G63 | HOSF (Triolein) | 296.6 |
| | Tripetroselenin | 184.6 |
| | tri-CLA | 190.7 |

The above data clearly indicate that tripetroselenin and tri-CLA are hydrolysed by lipolytic skin bacteria at least as readily as triolein and more readily in the case of S. epidermidis. This demonstrates that the population of bacteria commonly present on the underarm skin would be capable of hydrolysing triglycerides to release PPARα active free fatty acids locally onto the skin and thereby control or eliminate irritation.

Identification of Skin Benefit Agents by Keratinocyte differentiation Assay. Examples 6 and 7.

Background

Good skin condition results from the formation of an intact barrier that protects underlying tissues and prevents water loss. The stratum corneum that performs this barrier function is the end-product of keratinocyte differentiation normally. A crucial component of keratinocyte differentiation, and hence good skin condition, is the formation of cornified envelopes by the action of transglutaminase enzymes. Cornified envelopes are highly cross-linked cages encoated with covalently bound lipids and are considered to be vital for stratum corneum strength and water-impermeability. Molecules that are able to influence the maturation of keratinocytes, boosting transglutaminase activity and cornified envelopes formation are therefore potentially valuable actives for inclusion in formulations designed to improve skin condition. The assays for keratinocyte transglutaminase and cornified envelope are employed herein to identify skin benefit agents.

Method

Human foreskin keratinocytes (passage 3) were seeded at 4000 cells/well in 96 well plates in Keratinocyte Growth Medium (abbreviated to KGM) containing 0.03 mM calcium and grown for 3 days at 37° C. The cells were then treated with PPAR ligands in KGM containing 0.03 mM calcium for 4 days prior to harvest. Stock solutions of PPAR ligands were dissolved in dimethylsulphoxide (DMSO) and diluted in KGM before adding to the cells. The DMSO concentration was typically 0.01% and equivalent amounts of DMSO were added to the control cells. The harvested cells were washed 3× in phosphate buffered saline (PBS) and extracted in 1% Triton X100, 50 mM (tris[hydroxymethyl] aminomethane) (Tris) pH 8.0 plus protease inhibitors pepstatin and leupeptin (100 $\mu$l/well). The extract was assayed for DNA content using the Pico Green DNA assay (Molecular Probes, Inc.).

Transglutaminase (TGase) assay

The remaining cell debris attached to the 96 well plate was incubated with 70 $\mu$l/well of TGase assay buffer (50 mM Tris™ pH 8.0, 5 mM DTT, 50 mM $CaCl_2$, 150 mM NaCl, 15 $\mu$M Texas Red Cadaverine) and incubated for 16 hours at 37° C. The plates were then washed with distilled water (×2) and the fluorescence due to cross-linked Texas Red cadaverine was determined using excitation at 590 nm and emission of 645 nm.

Cornified Envelope Assay—Examples 8 and 9

Cells were grown in 96 well plates as described above for the TGase assay and the cornified envelopes were determined using a derivation of the Hough-Monroe & Milstone method (Anal. Biochem. 199, p25 (1991)). After Tris-triton extraction for TGase assay, the cells were extracted with 100 μl/well of 2% SDS, 20 mM DTT for 16 hours at 60° C. Once extracted the SDS suspension from each well was individually filtered through polyviylidenefluoride (PVDF) membrane (Immobilon-P™ Transfer Membrane, Millipore) which had been pre-blocked in Tris Buffered Saline (TBS) containing 0.5% (v/v) Tween 20, 0.5% using a Dot Blot TM Apparatus (Bio-Rad). Each sample was washed several times with TBS/Tween buffer before the membrane was removed from the apparatus, rinsed in distilled water and silver stained using silver stain kit (Bio-Rad). The stained dot blot membrane was scanned and analysed using Phoretix Array™ software.

EXAMPLE 6

This Example demonstrates Keratinocyte Transglutaminase Analysis using cis-9-trans-11-conjugated linoleic acid (CT-CLA).
Methods Cultured keratinocytes were treated with cis-9-trans-11-conjugated linoleic acid (CT-CLA) for 4 days. The cells were extracted with Tris-1% Triton X100™ and the non-extractable TGase activity associated with the cells was determined using Texas Red Cadaverine (in accordance with the methods described above). The values in the Tgase assay are summarised in Table 7 below.

TABLE 7

| μM CT-CLA | 30 μM Ca2 + TGase/ng DNA | | |
|---|---|---|---|
| | mean | sdev | n |
| 0 | 16.82 | 2.55 | 6 |
| 0.1 | 18.30 | 2.52 | 6 |
| 1 | 18.46 | 2.89 | 6 |
| 10 | 28.07 | 5.60 | 6 |

CT-CLA (10 λM) was found to significantly increase keratinocyte TGase activity as determined by 1 way ANOVA with Student-Neumann-Kuels multiple comparison (p<0.05). These results indicate that CT-CLA can enhance keratinocyte differentiation.

EXAMPLE 7

This example demonstrates Keratinocyte Transglutaminase Analysis using petroselinic acid.
Method The method of Example 6 was followed but using petroselinic acid instead of CT-CLA. The results of the assay are summarised in Table 8 below.

TABLE 8

| μM Petroselinic Acid | TGase activity (Arb. Units) | | |
|---|---|---|---|
| | mean | sdev | n |
| 0 | 285 | 136 | 6 |
| 0.01 | 366 | 54 | 6 |
| 0.05 | 563 | 107 | 6 |
| 0.1 | 471 | 172 | 6 |

TABLE 8-continued

| μM Petroselinic Acid | TGase activity (Arb. Units) | | |
|---|---|---|---|
| | mean | sdev | n |
| 1 | 752 | 77 | 6 |
| 5 | 743 | 98 | 6 |
| 10 | 741 | 158 | 6 |
| 15 | 729 | 208 | 6 |
| 25 | 907 | 263 | 6 |

Petroselinic acid (1–25 μM) was found to significantly increase keratinocyte TGase activity as determined by 1 way ANOVA with Student-Neumann-Kuels multiple comparison (p<0.05). These results indicate that petroselinic acid can enhance keratinocyte differentiation.

EXAMPLE 8

This example demonstrates Keratinocyte Cornified envelope analysis using pinoleic acid.
Methods Cultured keratinocytes were treated with pinoleic acid for 4 days. The cells were extracted with 2% SDS, 20 mM DTT and the cornified envelopes were quantified, after filtration using a PDVF membrane, by silver staining, as described above. The results of the assay are summarised in Table 9 below.

TABLE 9

| μM Pinolenic acid | Cornified envelopes assay (arb. Units) | | |
|---|---|---|---|
| | mean | sdev | n |
| 0 | 22831 | 6694 | 6 |
| 0.1 | 18828 | 1786 | 6 |
| 1 | 24860 | 4979 | 6 |
| 10 | 36579 | 9286 | 6 |

Pinolenic (10 μM) was found to significantly increase keratinocyte TGase activity as determined by 1 way ANOVA with Student-Neumann-Kuels multiple comparison (p<0.05). These results indicate that pinolenic acid can enhance keratinocyte differentiation.

EXAMPLE 9

This Example demonstrates Keratinocyte Cornified envelope analysis using hexadecatrienoic acid.
Methods The method of Example 8 was followed using hexadecatrienoic acid instead of pinoleic acid. The results are summarised in Table 10 below.

TABLE 10

| μM hexadeca-trienoic acid | Cornified envelopes assay (arb. Units) | | |
|---|---|---|---|
| | mean | sdev | n |
| 0 | 17996 | 8860 | 6 |
| 0.1 | 17617 | 3664 | 6 |
| 1 | 36017 | 15579 | 6 |
| 10 | 40997 | 8617 | 6 |

Hexadecatrienoic (1–10 μM) was found to significantly increase keratinocyte TGase activity as determined by 1 way ANOVA with Student-Neumann-Kuels multiple comparison (p<0.05). These results indicate that hexadecatrienoic acid can enhance keratinocyte differentiation.

EXAMPLE 10

This Example demonstrates Keratinocyte Proliferation Analysis using cis-9-trans-11-conjugated linoleic acid (CT-CLA).

Methods

Cultured keratinocytes were treated with cis-9-trans-11 conjugated linoleic acid (CT-CLA) for 4 days. The cells were extracted with Tris-1% Triton X100 and the DNA content per well was determine by the Pico Green assay in accordance with the above described procedure. The results are summarised in Table 11 below

TABLE 11

| µM CT-CLA | DNA (ng/well) | | |
|---|---|---|---|
| | mean | sdev | n |
| 0 | 92.17 | 11.69 | 6 |
| 0.1 | 81.83 | 6.08 | 6 |
| 1 | 81.33 | 9.18 | 6 |
| 10 | 59.50 | 5.13 | 6 |

CT-CLA (10 µM) was found to significantly reduce keratinocyte DNA synthesis activity as determined by 1 way ANOVA with Student-Neumann-Kuels multiple comparison (p<0.05). These results indicate that CT-CLA can act as a keratinocyte anti-proliferative agent.

EXAMPLE 11

This Example demonstrates Keratinocyte Proliferation Analysis using pinolenic acid.

Methods

The method of Example 10 was followed except that pinolenic acid was employed instead of CT-CLA. The results are summarised in Table 12 below.

TABLE 12

| µM Pinolenic acid | DNA (ng/well) | | |
|---|---|---|---|
| | mean | sdev | n |
| 0 | 14.46 | 0.58 | 6 |
| 0.1 | 13.41 | 0.35 | 6 |
| 1 | 12.95 | 0.63 | 6 |
| 10 | 12.63 | 0.33 | 6 |

Pinolenic (10 µM) was found to significantly reduce keratinocyte DNA synthesis activity as determined by 1 way ANOVA with Student-Neumann-Kuels multiple comparison (p<0.05). These results indicate that pinolenic can act as a keratinocyte anti-proliferative agent.

EXAMPLE 12

Keratinocyte Proliferation Analysis of cis-parinaric acid.

Methods

The method of Example 10 was followed except that cis-parinaric acid was employed instead of CT-CLA. The results are summarised in Table 13 below.

TABLE 13

| µM cis-Parinaric Acid | DNA (ng/well) | | |
|---|---|---|---|
| | mean | sdev | n |
| 0 | 3.5 | 0.4 | 6 |
| 1 | 3.3 | 0.9 | 6 |
| 5 | 4.1 | 0.8 | 6 |
| 10 | 2.6 | 0.4 | 6 |
| 20 | 1.5 | 0.4 | 6 |

Cis-parinaric (10 and 20 µM) was found to significantly reduce keratinocyte DNA synthesis activity as determined by 1 way ANOVA with Student-Neumann-Kuels multiple comparison (p<0.05). These results indicate that cis-parinaric can act as a keratinocyte anti-proliferative agent.

EXAMPLE 13

This Example employs Skin Organotypic Culture Analysis of Cis-parinaric acid to show anti-inflammatory action with antiperspirant induced irritation.

Methods

Skin organotypic cultures (Epiderm™, MatTek, USA) were treated topically with AP formulation of Example 2 and petroselinic acid was introduced in to the medium. The cultures were then incubated at 37° C., 5% $CO_2$, and 95% relative humidity (standard cell culture conditions) for 24 hours. The culture medium was assayed for the pro-inflammatory cytokine interleukin-6 (IL-6) and after washing to remove the AP formulation, the viability of the culture was determined using the MTT assay. IL-6 was determined using an ELISA assay (R&D systems). The results are summarised in Table 14 below.

TABLE 14

| Dose | IL-6 release (mean ± SD) | sd | Percentage of AP formulation value | n |
|---|---|---|---|---|
| Nil | 21.5 | 4.0 | 278.4 | 4 |
| AP | 57.1 | 24.7 | 100 | 4 |
| 1.0 µM cis-Parinaric Acid (+ AP) | 26.8 | 9.4 | 105.6 | 4 |
| 10.0 µM cis-Parinaric Acid (+ AP) | 23.3 | 5.3 | 81.5 | 4 |
| 100.0 µM cis-Parinaric Acid (+ AP) | 25.7 | 15.1 | 53.8 | 4 |

Cis-parinaric acid (1–100 µM) was found to significantly decrease AP-induced IL-6 release from the cultures using Dunnet's test with a significance value of p<0.05. The reduction in the pro-inflammatory cytokine IL-6 indicates that the cis-parinaric will inhibit AP-induced irritation. Culture viability of AP treatment alone was not significantly different from those of AP and cis-parinaric acid treatment.

EXAMPLE 14

This Example demonstrates Keratinocyte Proliferation Analysis using hexadecatrienoic acid.

Methods

The method of Example 10 was followed except that hexadecatrienoic acid was employed instead of cis9 transit conjugated linoleic acid. The results are summarised in Table 15 below.

TABLE 15

| μM hexadeca-trienoic acid | DNA (ng/well) | | |
| --- | --- | --- | --- |
| | mean | sdev | n |
| 0 | 1.66 | 0.19 | 6 |
| 0.1 | 0.98 | 0.23 | 6 |
| 1 | 1.27 | 0.19 | 6 |
| 10 | 1.13 | 0.26 | 6 |

Hexadecatrienoic (0.1–10 μM) was found to significantly reduce keratinocyte DNA synthesis activity as determined by 1 way ANOVA with Student-Neumann-Kuels multiple comparison (p<0.05). These results indicate that hexadecatrienoic can act as a keratinocyte anti-proliferative agent.

We claim:

1. An antiperspirant cosmetic composition suitable for topical application to the human skin, comprising:
   i. an antiperspirant active comprising an astringent aluminium or zirconium salt;
   ii. a carrier for the antiperspirant active; and
   iii. either (a) a PPAR activating fatty acid other than at least 1% by weight of ricinoleic acid or linoleic acid or (b) a hydrolysable precursor of a PPAR activating fatty acid other than borage oil, castor oil or sunflower seed oil
       in an effective amount that is insufficient to gel the composition by itself.

2. A composition according to claim 1 in which the hydrolysable precursor comprises a triglyceride or ester of the PPAR activating fatty acid.

3. A composition according to claim 1 in which the PPAR activating fatty acid is olefinically unsaturated.

4. A composition according to claim 1 in which the PPAR activating fatty acid is selected from petroselinic acid, cis-9-trans-11 conjugated linoleic acid, trans-10-cis-12 conjugated linoleic acid, 7-trans octadecanoic acid, cis-parinaric acid, docosahexenoic acid, cis-4,7,10,13,16,19 docosahexenoic acid, ricinolaidic acid, stearidonic acid, columbinic acid, linolenelaidic acid, vaccenic acid, eicosapentanoic acid, and pinolenic acid, incorporated as such or in a hydrolysable precursor thereof.

5. A composition according to claim 4 which contains a triglyceride-containing oil selected from coriander seed oil, balsimina seed oil, parinarium laurinarium kernel fat or sabastiana brasilinensis seed oil, dehydrated castor seed oil, and aquilegia vulgaris oil.

6. A composition according to claim 4 in which the PPAR activating fatty acid contains 16 or 18 carbon atoms.

7. A composition according to claim 6 in which the PPAR activating fatty acid comprises petroselinic acid.

8. A composition according to claim 5 in which it contains coriander seed oil.

9. A composition according to claim 1 which comprises from 0.1 to 20% by weight and preferably 0.5 to 10% by weight of the PPAR activating fatty acid or hydrolysable precursor thereof.

10. A composition according to claim 1 which employs a combination of the PPAR activating fatty acids or their precursors in a weight ratio of from 5:1 to 1:5.

11. A composition according to claim 1 in which it comprises from 10 to 30% by weight antiperspirant active.

12. A composition according to claim 1 in which the antiperspirant active contains aluminium chlorohydrate and/or aluminium/zirconium glycine complex.

13. A composition according to claim 1 which comprises a volatile silicone carrier, preferably in an amount of from 10 to 70 wt %.

14. A composition according to claim 1 which comprises a structurant or thickening agent in a concentration sufficient to produce a firm stick or a soft solid.

15. A composition according to claim 1 in which comprises base composition which forms an aerosol composition together with a propellant, the weight ratio of propellant to base composition being selected within the range of from 40:60 to 99:1.

16. A method of reducing or eliminating skin irritancy arising from topical application of an antiperspirant cosmetic composition comprising an antiperspirant active comprising an astringent aluminium or zirconium salt and a carrier for the antiperspirant active which comprises the step of incorporating in the composition an effective amount of either (a) a PPAR activating fatty acid a) a PPAR activating fatty acid excluding at least 1% by weight of ricinoleic acid or linoleic acid or (b) a hydrolysable precursor of a PPAR activating fatty acid other than borage oil, castor oil or sunflower seed oil that is insufficient to gel said composition.

17. A method of reducing or eliminating sweat or body odour comprising applying topically to human skin a composition according to claim 1.

18. A method of reducing or eliminating skin irritancy arising from topical application of an antiperspirant cosmetic composition comprising an antiperspirant active comprising an astringent aluminium or zirconium salt and a carrier for the antiperspirant active which comprises the step of incorporating in the composition a PPAR activating fatty acid other than ∝-linolenic acid or hydrolysable precursor thereof in an amount that is sufficient to reduce skin irritancy and insufficient to gel the composition.

* * * * *